United States Patent [19]

Neway et al.

[11] Patent Number: 5,336,666
[45] Date of Patent: Aug. 9, 1994

[54] IMMUNOSTIMULANT DRUG BASED ON POLAR GLYOPEPTIDOLIPIDS OF MYCOBACTERIUM CHELONAE

[76] Inventors: Tsehay Neway, 14, rue Jean-Pierre-Laurens, F-92260 Fontenay-aux-Roses, France; Charles Pilet, 8, avenue du Buisson, F-94100 St. Maur, France

[21] Appl. No.: 828,855

[22] PCT Filed: Jun. 6, 1991

[86] PCT No.: PCT/FR91/00449
§ 371 Date: Apr. 3, 1992
§ 102(e) Date: Apr. 3, 1992

[87] PCT Pub. No.: WO91/18617
PCT Pub. Date: Dec. 12, 1991

[30] Foreign Application Priority Data
Jun. 6, 1990 [FR] France .................. 90 06997

[51] Int. Cl.⁵ .................. A61K 37/10; A61K 37/02
[52] U.S. Cl. .................. 424/282.1; 514/9; 514/21; 514/23; 514/61; 514/8; 530/322; 530/344; 530/345; 435/863
[58] Field of Search .................. 514/8, 9, 21, 23, 61; 530/322, 344, 345; 424/92; 435/863

[56] References Cited
PUBLICATIONS

Tsang et al., *Int. J. Syst. Bacteriol.*, vol. 34, No. 1, pp. 35–44, Jan. 1984.
Brennan et al., *J. Biol. Chem.*, vol. 254, No. 10, pp. 4205–4211, May 25, 1979.
T. Neway et al.: "Immunomodulatory properties of a strain of mycobacterium chelonae I. Mouse lymphocyte responses in vitro", Biological Abstracts, vol. 89, No. 1, Ref. No. 4236, Jan. 1990 (Phila., Pa.).
A. Y. Tsang et al.: "Antigenic relationships of the mycobacterium fortuitum–mycobacterium chelonae complex", Chemical Abstracts, vol. 100, No. 17, Apr. 23, 1984 (Columbus Ohio).
P. E. Brownback et al.: "Modified lymphocyte response to mitogens after intraperitoneal injection of glycopeptidolipid antigens from mycobacterium avium complex", Injection & Immunity, vol. 56, No. 5, May 1988, (Washington, D.C.).

*Primary Examiner*—Michael G. Wityshyn
*Assistant Examiner*—Abdel A. Mohamed
*Attorney, Agent, or Firm*—Wegner, Cantor, Mueller & Player

[57] ABSTRACT

A pharmaceutical composition having as the active ingredient an at least partially purified extraction fraction of polar glycopeptidolipids of *Mycobacterium chelonae* having formula (1). The composition can be used in particular for stimulating non-specific immunity in humans and animals.

18 Claims, No Drawings

IMMUNOSTIMULANT DRUG BASED ON POLAR GLYOPEPTIDOLIPIDS OF MYCOBACTERIUM CHELONAE

FIELD OF THE INVENTION

The invention relates to a novel immunostimulant drug having as active ingredients polar glycopeptidolipids (pGPL) of *Mycobacterium chelonae*.

BACKGROUND OF THE INVENTION

The invention relates to a novel immunostimulant drug having as active ingredients polar glycopeptidolipids (pGPL) of *Mycobacterium chelonae*.

It is known that pGPL, present in the cell wall of atypical Mycobacteria, have high species-specificity.

Glycopeptidolipids (GPL) are compounds which combine fatty acids, peptides, and sugars.

Extensive studies of GPL have been carried out with the aim of classifying and identifying Mycobacteria.

Investigators have shown a decrease in the proliferative response induced by nonspecific mitogens, in splenocytes of mice treated with *Mycobacterium avium* pGPL (see Brownback and Barrow, *Infection and Immunity*, 56, 1044–1050 (1988)). The same investigators showed a decrease in the proliferative response of these cells when the cells are co-stimulated in vitro with the aforesaid pGPL and mitogens.

Immunostimulant properties of living *M. chelonae* on the immunocompetent cells have been demonstrated (see Biozzi et al., *Rev. Franc. Etudes Clin. Biol.*, 5, 867–890 (1960); Pilet and Goret, *J. Reticuloendoth Soc.*, 3, 305–309 (1966); al., *Comp. Immunol. Infect. Dis.*, 12, 63–70 (1989)).

SUMMARY OF THE INVENTION

It has been discovered, in connection with the present invention, that PGPL of *M. chelonae* has immunostimulant properties, in contrast to *M. avium*, the latter which does not have such properties.

It is known that GPL of most atypical Mycobacteria have in common the following structure:

Phe—aThr—Ala—Alaninol, wherein the N-terminal amino group of the Phe is acylated by a long-chain fatty acid, the alaninol group is connected to a sugar, and the allo-threonine group (aThr) is either connected to a sugar (in the case of a non-polar GPL) or to an oligosaccharide (in the case of a PGPL). This glycopeptidolipid structure is the same, in particular, in all Mycobacteria in the MAIS complex (Mycobacterium avium intracellulare scrofulaceum) and in the two subspecies of *Mycobacterium chelonae* (see Brennan and Goren, *J. Biol. Chem.*, 254, 4205–4211 (1979); Brennan, *Rev. Infect. Dis.*, 3, 905–913 (1981); Brennan, *The Mycobacteria: A Source Book*, Part A, Kubica and Wayne Eds., Marcel Dekker, New York and Basel, 467–489 ( 1984 ); Tsang et al., *Int. J. Syst. Bacteriol.*, 34, 35–44; and Asselineau and Asselineau, *The Mycobacteria: A Source Book*, Kubica and Wayne Eds., Marcel Dekker, New York and Basel, pp. 345–360, ( 1984 ).

The pGPL of *M. chelonae* were described by Tsang et al., loc. cit. Because the species variations of pGPL in atypical Mycobacteria relate to the osidic part, the same authors studied the osidic part in *M. chelonae*, and they proposed the following structure for the oligosaccharide: 3,4-di-O-methylrhamnose-(1→?)-rhamnose-(α-1→2)-6-deoxytalose.

pGPL have been used in the identification and differentiation of *M. chelonae* in the complex *M. fortuitum-M. chelonae*, by thin layer chromatography (Tsang et al., loc. cit. ), and by the ELISA method (Yanagihara et al., 1985 *J. Clin. Microbiol.*, 21, 569–574).

Basically, the pGPL of *M. chelonae* correspond to formula 1:

$$R-CO-NH-D-Phe-D\text{-}aThr-D-Ala-L\text{-}Alaninol\text{-}O\text{-}sugar \quad (1)$$
$$|$$
$$O$$
$$|$$
$$oligosaccharide,$$

wherein
Phe represents phenylalanine,
aThr represents allo-threonine,
Ala represents alanine,
sugar is 3,4-di-O-methyl rhamnose,
the oligosaccharide has the following structure: 3,4-di-O-methylrhamnose-rhamnose-6-deoxytalose, and
R—CO— is the acyl group of a fatty acid,
wherein the 3,4-di-O-methylrhamnose groups are connected by a glycosidic link to the aThr and the alaninol, respectively, and wherein the C-terminal COOH group of the alanine is connected to the alaninol by an amide linkage.

The most accurate structure for the oligosaccharide is that given by Tsang et al., as indicated above, but in it the position of the link between the rhamnose and the dimethylrhamnose is not known.

In natural pGPL, the sugars of the oligosaccharide part are acetylated.

In the pGPL of *M. chelonae*, as in the GPL of other Mycobacteria, the nature of the fatty acids depends on the culture medium, the temperature, and the duration of the culture (see, e.g., Ratledge, 1982, "Lipids: Cell Composition, Fatty Acid Biosyntheses" in "The Biology of the Mycobacteria" Vol 1 Ratledge and Stanford Eds., Academic Press, London ( 1982 ), pages 53–93; and the references cited supra).

The natural pGPL are in fact mixtures of components of formula 1, wherein the fatty acid acyl group R—CO— is variable. These fatty acids have at least 16 C atoms, and generally less than 36 C atoms.

Accordingly, the principle claimed matter of the present invention comprises an immunostimulant drug containing as active ingredient at least one GPLp of *M. chelonae*, or a derivative of pGPL of *M. chelonae* which derivative is active as an immunostimulant.

The pGPL present in the drug according to the invention may comprise extraction fractions, at least partially purified, of GPL from the cell wall of *M. chelonae*, obtained according to known methods, provided that the invention does not extend to drugs comprising, as the sole source of pGPL from *M. chelonae*: live or killed *M. chelonae*, or entire cell walls or fragments of cell walls of *M. chelonae*.

The extraction fractions, at least partially purified, of pGPL, which fractions are employed as active ingredients in the drugs according to the invention, may be extracts of GPL from the from the cell walls of *M. chelonae*, which extracts are soluble in, e.g., cold methanol (in particular, methanol at +4° C.).

These are, in particular, GPL fractions which can be obtained by extraction from cells or cell walls of *M. chelonae* with the aid of a mixture of chloroform and methanol in the ratio 2:1, at 18°–50° C., and which fractions are soluble in cold methanol, e.g., they remain soluble after addition of cold methanol (4° C) such that the ratio (by volume) of methanol to chloroform is at least 5:1. These fractions may also be obtained by extraction as indicated supra followed by purification by column chromatography over silica gel.

A particular object of the invention is a drug comprising, as active ingredient, at least one compound of formula 1, or an active derivative of same.

The pGPL present in the drugs according to the invention need not be merely naturally acetylated pGPL but may also be active derivatives of pGPL, in particular the corresponding de-acetylated derivatives.

The pGPL or derivatives of pGPL comprising the active ingredient of the drugs according to the invention may be prepared from cultures of *M. chelonae*.

Cultures of *M. chelonae* may be obtained from public collections as follows:

NCTC (Nat. Collection of Type Cultures) (U.K.), Deposit No. 946 (*M. chelonae* subsp. *chelonae*);

ATCC (Amer. Type Culture Collection) (U.S.), Deposit No. 19977 (*M. chelonae* subsp. *abscessus*);

CIPT (Collection Institut Pasteur Tuberculose) (Paris, France), Deposit No. 140420019 (*M. chelonae* subsp. *chelonae*);

CIPT (Collection Institut Pasteur Tuberculose) (Paris, France), Deposit No. 140420020 (*M. chelonae* subsp. *abscessus*).

*M. chelonae* can be maintained in Lowenstein-Jensen medium (Institut Pasteur, of Paris), and can be cultivated in Sauton medium placed in Roux bottles following solidification by addition of 1.5% of Bacto-agar (Difco). *M. chelonae* can also be cultivated in fermentation apparatus or with the aid of film cultures, or by any other similar method.

The method of extraction of pGPL from *M. chelonae* is known per se, as mentioned above. It consists of extracting the totality of the lipid complexes from the living or killed bacteria or from the bacterial wall. The extraction may be accomplished with the aid of, e.g., mixtures of chloroform and methanol, in contact with the bacteria or lyophilized bacteria.

Then one can at least partially eliminate the glycolipids, the carotenoids, and the free lipids. For example, one can proceed by adding large quantities of cold methanol to a solution of all of the lipid complexes in chloroform. This causes precipitation of some of the glycolipids, carotenoids, and free lipids. The pGPL and apolar GPL, the phospholipids, and the remaining free lipids remain in solution.

At this stage it is useful to proceed, in known fashion, with de-acetylation by treatment with diluted or mild alkali (addition of a solution of NaOH in methanol). For example, a 0.2 M solution of NaOH in methanol is added to the lipid complexes from the preceding step which complexes are in solution in a mixture (2:1) of chloroform and methanol, wherein the volume of the NaOH-methanol solution added is equal to the volume of the solution of lipid complexes. The de-acetylation is specific to the GPL of the Mycobacteria, which resist degradation further beyond de-acetylation, while the other lipids, which one wishes to eliminate (phospholipids, carotenoids, and other undesirable lipids) are degraded. The de-acetylation thus facilitates the separation and further purification of the desired GPL by column- or thin layer chromatography. After the alkaline treatment, the mixture is neutralized with an acid, e.g., concentrated acetic acid. It is advantageous at this stage to wash the organic phase with a mixture of chloroform, methanol, and water (4:2:1) or a similar mixture. The washed organic phase can then be subjected to purification by column chromatography, or by the method of Tsang et al., loc. cit., or the method of Dimitrijevich et al., *J. Chromato.*, 377, 345–349 (1986).

In this way a partially purified fraction is obtained which contains the pGPL of *M. chelonae*. The column chromatography enables one to separate the following: those undesirable lipids which may have escaped degradation by the alkaline treatment, the pGPL, and (if any) the glycolipids containing trehalose (which are present in the case where the precipitation with cold methanol has not been carried out).

The apolar glycopeptidolipids of *M. chelonae* are fractions near the solvent front, and are colored pinkish yellow by orcinol in a test of TLC. They are not specific to the species (see, e.g., Tsang et al., loc. cit.).

The pGPL of *M. chelonae*, which are species-specific, are fractions which are distant from the solvent front, and are colored maroon with a gold tint in the case of *M. chelonae* subsp. *chelonae* and dark orange in the case of *M. chelonae* subsp. *abscessus*, in a test with orcinol in thin layer chromatography (TLC) (see, e.g., Tsang et al., loc. cit.).

The active ingredient of the compositions according to the invention may also be at least one compound of formula 1, obtained by synthesis or semi-synthesis, according to the classical techniques of peptide and saccharide synthesis.

The composition according to the invention is prepared according to the conventional galenic methods.

The pGPL or extraction fractions containing them may be subjected to the action of ultrasound for 20–50 min, with a wavelength of 8 microns and a concentration of pGPL of 1–20 mg/ml, in a suitable liquid vehicle, to homogenize the product.

The active ingredient (pGPL) in the compositions according to the invention is generally present in the amount of 0.07–8% by weight, based on the total weight of the composition.

The compositions according to the invention may be offered, in particular, as a suspension in a suitable liquid pharmaceutical vehicle. The suspension may contain a pharmaceutically usable surfactant, particularly a nonionic surfactant such as sorbitan polyoxyethylene monooleate (e.g. Tween ® 80) The liquid compositions may be subjected to lyophilization (freeze-drying), optionally with addition of a lyophilization agent, and may be stored in lyophilized form and reconstituted at the time of use. The liquid composition when ready for use generally contains 0.2–80 mg/ml pGPL (depending on the mode of admininstration employed).

The suspension may also contain up to 0.2 vol % of surfactant. The compositions according to the invention may generally contain an efficacious quantity of a customary preservative, e.g. merthiolate.

The compositions according to the invention may be, in particular, compositions in the form of potable or injectable suspensions, or for topical application, or compositions for administration by nose or conjunctiva.

The compositions according to the invention may also be offered in the form of gel capsules, tablets, powders, suppositories, gingival pastes, or creams.

As will be seen in the experimental section infra, the pGPL of *M. chelonae* are stimulants of nonspecific defenses of the organism. They can also nonspecifically stimulate a specific immune reaction (auxiliary effect).

The composition according to the invention is thus usable as an immunostimulant drug, in humans or animals. It is also usable, in particular, as an adjuvant to promote immunity conferred by vaccines, and as a potentiator of antibiotic therapy.

The composition according to the invention may also be used as a growth- and/or anabolic factor in animals and humans.

It may be administered, in particular, by a parenteral mode (e.g. intra-peritoneal, subcutaneous, intra-muscular, intravenous, percutaneous), by mouth, nasally, conjunctivally, rectally, or perlingually.

It may also be used topically, with the aid of gingival pastes, or tablets which disintegrate when held buccally, particularly in nonspecific immunotherapy of disorders of the buccal cavity (dental alveolar pyorrhea, gingivitis, peridontitis, etc.).

Usual posology may be, e.g., 0.1-12, preferably 0.5-10 mg/kg body weight per day, in one or more administrations. E.g., most frequent dosages are 0.5-3 mg/kg for parenteral administration, 4-10 mg/kg for by mouth, and 2-4 mg/kg for nasal administration. The drug according to the invention is administered at an effective dose, particularly as an immunostimulant treatment, in the case of secondary immune deficiency; as an adjunct treatment in local or systemic infectious diseases; as an adjunct treatment in AIDS, particularly in association with antiviral treatments; as an adjunct treatment in cases of parasitic diseases or cancerous conditions; and as a corrective treatment for immunosuppressive effects (particularly those evidenced by leukopenia) of anticancer therapies.

The drug according to the invention may also be administered as a prophylactic, in the various cases mentioned above, particularly for prevention of recurrent infections in the otorhinolaryngology area, and for prevention of hazards of infection in chronic disease conditions, as well as as an adjuvant in vaccines.

It may also be used to promote increased or decreased weight in animals and humans.

The pGPL of *M. chelonae* may be used, in particular, as feed additives for animals, intended to promote growth and/or resistance to infection.

A further element of the principal claimed matter of the invention is use of pGPL of *M. chelonae*, such as described supra, as active ingredients in preparation of a nonspecific immunostimulant drug or an anabolic drug, or as an adjuvant in preparing a vaccine, or in the preparation of a nutrient composition.

The invention relates in particular to the use of pGPL of *M. chelonae* as active ingredients in the preparation of a nonspecific immunostimulant drug intended in particular to correct the immunosuppressive effects (e.g. chemically induced leukopenia) of anticancer therapies.

The following Examples illustrate the invention without limiting it in any way:

EXAMPLE 1:

Purification of a Fraction Comprising gPLP of *M. Chelonae*: Culturing the Bacteria

*Mycobacterium chelonae* subsp. *chelonae* are cultured at 35° C. in the media indicated supra, until steady state, and are then collected and washed by centrifugation at 5600 x g. The cells were then dried or lyophilized and were subjected to extraction within the shortest possible time thereafter.

Extraction of All Lipid Compounds

Extraction of the total lipids from the cell walls of *M. chelonae* is carried out by a technique similar to that described by Brennan and Goren, *J. Biol. Chem.*, Vol. 254, No. 10, 4205–4211 (1979).

The extraction employs a 2:1 chloroform:methanol mixture, in the amount of 40 ml mixture per gram lyophilized Mycobacteria, at 50° C. for 18 hr in a flask immersed in a hot water bath. The extract is recovered by filtration through Whatman No. 3 paper. The residue is subjected to a second extraction by the same method but lasting only 4 hr. The extracts are combined and the solvents were evaporated. The dry extract is stored at +4° C. until the following step.

Elimination of Glycolipids, Carotenoids, and Free Lipids

The total-lipids complexes are solubilized with a sufficient quantity of chloroform, and a substantial quantity of methanol is added at +4° C. A precipitation is observed. The quantity of methanol should be sufficient such that addition of further methanol does not bring about further precipitation. The precipitate contains glycolipids, carotenoids, and free lipids. The pGPL, the apolar GPL, the phospholipids, and the other free lipids remained in solution.

The precipitate is removed by centrifuging, then the solvents of the supernatant is evaporated.

De-acetylation and Washing

The residue obtained from evaporation of the product in the preceding stage is subjected to a mild alkali treatment (de-acetylation), and the resulting mixture is washed with a mixture of chloroform, methanol, and water.

For this purpose, the residue obtained from the preceding stage is taken up again in a 2:1 chloroform:methanol mixture, and an equal volume of 0.2 M NaOH solution in methanol is added. After 30 min at 37° C., the mixture is neutralized with 12 5 µl/ml concentrated acetic acid, followed by washing. The washing mixture was 4:2:1 chloroform:methanol:water. After agitation, and release of the gas which was produced, the mixture is allowed to sit 1 hr. The aqueous phase is discarded, and the organic phase is drawn off and subjected to evaporation. The residue is stored at 4° C.

Separation and Purification of the GPL By Column Chromatography Over Silica Gel A glass column is prepared, containing 100 g silica gel 60 (particle size 0.063-0.200 ram) per g lipids complex. The method is as in Tsang et al., loc. cit., wherein the constituents are separated by using an increasing percentage of methanol in the chloroform, beginning with pure chloroform. It may also be possible to use the method of Dimitrijevich et al., loc. cit., wherein the chromatography is carried out with a fixed percentage of methanol (10%) in chloroform. The flow rate is fixed at about 1.5 ml/min. The fractions are analyzed by analytical TLC. Fractions of the same mobility are combined, weighed, and saved, preferably at 4° C.

Thin Layer Chromatography (TLC)

TLC plates (glass plates 20×20 cm and 1 mm thickness) (Merck) are used, activated by heating at 110° C. for 30 minutes prior to use.

The fractions obtained in the preceding step are adjusted to 10 mg/ml in a 2:1 chloroform:methanol mixture. The preparations are then deposited on equidistant spots (with minimum separation of 1 cm) at 1–2 cm from the lower edge of the plate. The spots are formed with the aid of Pasteur pipettes with ends drawn out and curved. The plates are then placed in a tray containing the migration solvent (60:12:1/chloroform:methanol:water). When the solvent has migrated to 1 or 2 cm below the upper edge of the plate, the migration is terminated. The plate is dried in a ventilated hood, and the developing reagent is sprayed on. The reagent for pGPL is 0.1% pulverized orcinol in a 40% solution of sulfuric acid in double distilled water. After heating 3–10 min in a heating cabinet at 110°–130° C., the specific pGPL of M. chelonae are colored maroon with a gold tint, whereas the apolar glycopeptidolipids is colored pinkish yellow. The chromatography allows one to monitor the degree of purity of the isolated extract.

For identification and monitoring of purity of the pGPL, the following analytical methods may be used:

Acid Hydrolysis with 1 N HCL

Acid hydrolysis of specific pGPL of M. chelonae in the presence of 1 N HCl enables liberation of specific sugars (methylrhamnose, rhamnose, and deoxytalose) which can be identified by paper chromatography (on Whatman No. 1) and by gas phase chromatography.

Acid Hydrolysis with 6 N HCL

Acid hydrolysis with 6 N HCl, of the residue of the preceding stage, enables liberation of the specific amino acids of GPL of Mycobacteria, which amino acids can be identified by TLC. In the case of M. chelonae, as in the case of atypical Mycobacteria these amino acids are phenylalanine, alanine, alaninol, and allothreonine.

Analysis of GPLP by IR Spectra

Analysis of de-acetylated pGPL of M. chelonae showed the characteristic peaks of peptide links of the glycopeptidolipids, analogous to those described by Brennan and Goren, 1979, loc. cit., and by Brennan, 1984, loc. cit.

EXAMPLE 2

Preparation of an Injectable Suspension

The pGPL obtained in Example 1 are taken up again in chloroform and evaporated twice under nitrogen atmosphere, in an ultrasonic treatment tube.

The residue is suspended in a liquid suitable for preparation of injectable solutions such as physiological serum (e.g. apyrogenic 8.5% NaCl solution). One may also add a surfactant compatible with parenteral administration, e.g. Tween ® 80, in the amount of 0.1–0.2 vol %. The purpose of adding this surfactant is to facilitate the suspending of the materials.

The suspension thus obtained is then subjected to ultrasonic treatment for about 20–50 min, at amplitude 8 microns, with concentration of pGPL of 1–20 mg/ml, with the aim of homogenizing the product.

Injectable suspensions may also be prepared with other acceptable media, such as standard phosphate buffer or similar media.

The concentration of the pGPL is adjusted to, e.g., between 0.2 and 80 mg/ml, depending on the application. For extended storage, the preparation may be lyophilized and then reconstituted in the physiological serum without appreciable loss of activity.

EXAMPLE 3

Pharmacological Tests of pGPL of M Chelonae

These tests were carried out with the pGPL obtained in Example 1.

1. Stimulative effect for lymphoblastic transformation

This effect is evaluated by direct effect on the cells (by the increase in lymphoblastic transformation of splenocytes and thymocytes in mice previously treated with pGPL of M. chelonae), or by indirect effect (increase in proliferative response to mitogens). These effects are measured via incorporation of tritiated thymidine.

The tests is carried out on female Balb/c mice.

The product is administered by mouth at 12 mg/kg or s.c. at 2.5 mg/kg, in a course of 4 administrations, each given 3 days apart (for the p.o.) or 3 administrations 3 da apart (for the subcutaneous), to groups of 5 animals. The control groups are treated with the solvent alone.

Results

The pGPL stimulates the lymphoblastic transformation of mouse splenocytes in subcutaneous treatment ($P \leq 0.001$) and by oral treatment ($P \leq 0.05$).

The response of mouse splenocytes to mitogens is increased in subcutaneous stimulation, for: concanavalin A (ConA; IBF-LKB) ($P \leq 0.02$); phytohemagglutinin (PHA; Difco) ($P \leq 0.01$); and lipopolysaccharide B (LPS, Difco) ($P \leq 0.001$). Such increase was also observed in oral stimulation, for the same 3 mitogens ($P \leq 0.001$ for ConA, PHA and LPS).

The response of mouse thymocytes to mitogens was also increased very significantly, for concanavalin A and LPS ($P \leq 0,001$ for ConA, PHA and LPS).

2. Capacity of induction of monokines by peritoneal macrophages of treated Balb/c mice:

When the macrophages are contacted with an antigen or mitogen having immunostimulant effects, they respond by a secretion of monokines (interleukin-1, and tumor necrosis factor, TNF). The test for induction of monokines by the peritoneal macrophages is thus a means of evaluation of the effects of immunostimulant products on these cells.

Results

The activation, with LPS, of peritoneal macrophages from mice previously treated with pGPL show a very significant induction of interleukin-1 (IL-1) activity (equivalent of 107 units/ml) in the transformation of thymocytes of C3H/Hej mice (mice not sensitive to LPS).

The supernatant of these macrophages also had a toxic effect on cells of the tumor line L929, which are sensitive to the action of TNF (a quantity equivalent to 20000 units/ml).

The i.p. stimulation of Balb/c mice by pGPL at a dose of 2.5 mg/kg given in each of 3 administrations at 3-day intervals resulted in significant induction of TNF activity in the serum of these animals, evaluated by the toxicity to cells of the tumor line L929 (toxicity corresponded to a quantity of TNF equivalent to 34000 units/ml).

3. Capacity for induction of lymphokines by Balb/c mouse splenocyte

When the splenocytes are contacted, in vivo or in vitro, with an antigen or mitogen having immunostimulant effects, they respond by a secretion of lymphokines.

The best known of the lymphokines is interleukin-2 (IL-2), which is indispensable for the survival and multiplication of a line of IL-2 dependent cytotoxic T lymphocytes (mouse thymome) (CTLL-2).

Results

The subcutaneous stimulation, with pGPL, of Balb/c mice with 2.5 mg/kg doses (in each of 3 administrations at 3-day intervals) provided a significant indication of the IL-2 activity measured in the supernatant of splenocytes after 48 hr (quantity equivalent to 5.55 units/ml).

4. Tests of delayed hypersensitivity in mice

The delayed hypersensitivity reaction (HSR) is triggered by a locally injected allergen (in plantar cushions) following initial intravenous sensitization. If the animal is treated with a nonspecific immunostimulant acting on the T lymphocytes, one observes increased delayed hypersensitivity when the allergen is introduced locally the second time.

In this test, the increase in volume of the plantar cushions following the second injection of the allergen is analyzed. The allergen used was sheep erythrocytes. These were injected intravenously two days after the last stimulation of the mice by the product studied (intra-peritoneally or subcutaneously) and four days before the test of DHR. The stimulated mice received the test product (intra-peritoneal. or subcutaneous. ) in doses of 2.5 mg/kg on each of days −8, −5, and −2. The control mice received only normal saline. On day zero, all of the mice receive, intravenously, a single dose of 1 million sheep erythrocytes. On day +4, the mice received $10^8$ sheep erythrocytes, injected into the plantar cushions.

Results

The intra-peritoneal and subcutaneous stimulation of C57BL/6 mice, by the product administered 3 times separated by 3-day intervals, caused increased DHR ($P<0.001$) with respect to the control mice (excepting one reading at 72 hr), at levels of increase comparable to that caused by BCG.

5. Increase in antibody response of mice to sheep erythrocytes

The degree of the antibody response depends on the nature of the antigen and the nature and condition of the immune system. When the immune system is stimulated by an immunostimulant, or by an antigen in the presence of an adjuvant, the antibody response is increased. In the tests which were conducted, this property of pGPL was analyzed by the antibody response of C47BL/6 mice to sheep erythrocytes, when the mice were previously stimulated with the test product. The treated mice received the test product intraperitoneally and subcutaneously, in doses of 2.5 mg/kg on each of days −8, −5, and −2. The control mice received only physiological serum.

On day zero, each of the mice receive a single intravenous dose of $10^6$ sheep erythrocytes. Sera were then sampled on days zero to +43, and these were tested for ability to hemolyze sheep erythrocytes.

Results

The intravenous and subcutaneous stimulation of C57BL/6 mice with pGPL in 3 administrations with 3-day intervals in between resulted in very significant increases of the antibody response to sheep erythrocytes, for the serum samples taken on days 7, 11, and 25 in the case of intra-peritoneal stimulation, and for the serum samples taken on days 7, 20, and 25 in the case of subcutaneous stimulation.

6. Tests of systemic protection a) Test of protection against infection by Klebsiella pneumoniae in mice:

The intra-peritoneal injection of K. pneumoniae specially adapted to mice causes fatal septicemia within 24–48 hr.

The tests consist in determining the survival time of treated mice, in comparison to that of controls. The treated mice receive the test product in intra-peritoneal doses of 2.5 mg/kg on each of days −8, −5, and −2. The control mice received only physiological serum. On day zero, all of the mice received one suitable intraperitoneal dose of K. pneumoniae. Mortality during the subsequent 5 days was then observed.

Results

The intra-peritoneal stimulation with pGPL, in doses of 2.5 mg/kg for each of 3 administrations with 3-day intervals in between, very significantly protected the CDI mice infected with $50 \times LD50$ of K. pneumoniae. In fact, the animals showed no signs of disease during the test.

b) Protection against leukemia induced by injection of L 1210 cells in mice:

The test consists of determining the survival time of treated B6D2/F1 mice, over that of control mice.

The L-1210 leukemia cells were cultivated in a suitable medium, prior to the test.

The treated mice receive the test product in intra-peritoneal doses of 2.5 mg/kg on each of days −8, −5, and −2. The control mice receive only physiological serum. On day zero, each of the mice receive one intraperitoneal dose of $10^6$ viable L-1260 cells. The survival time are determined.

Results

The intra-peritoneal stimulation with pGPL, in doses of 2.5 mg/kg for each of 3 administrations with 3-day intervals in between, very significantly prolonged the survival time of the B6D2/F1 mice inoculated with L-1210 leukemia cells, the prolongation being 33% with respect to the survival of the control mice.

7. Evaluation of the anabolic effect in subcutaneous administration to mice

The product was injected sub-cutaneously at a dose of about 2.5 mg/kg in each of 3 administrations at intervals of 3 days. The weights of the mice were recorded daily for 10 days, and the total weight gain was evaluated.

The treated mice received the pGPL in doses of 2.5 mg/kg on each of days −10, −7, and −4. The control mice received only physiological serum.

Results

The subcutaneous stimulation with pGPL at doses of 2.5 mg/kg in each of 3 administrations at intervals of 3 days had significant anabolic effects in the Balb/c mice ($P \leq 0.02$).

8. Anti-leukopenia effect of pGPL in chemically induced leukopenia in mice

The test consists of first inducing a depletion of leukocytes in mice with the aid of Adriblastine (doxorubicin chlorhydrate lactose, a cytostatic product in the group of anthracyclines). Later, the same mice are treated with pGPL and other products used as positive controls (GM-CSF of mice, supplied by Genzyme) until these blood cells are restored to normal level.

The Balb/c mice are treated with Adriblastine intravenous in the amount of 5 mg/kg/da (volume 50 μL), on each of days zero and +1. The same mice then received the pGPL, the GM-CSF, or physiological serum, in a volume of 0.15 ml. The treatment was administered on days 2, 5, 8, 11, 14, 17, and 20. Counts of circulating leukocytes were carried out on each animal on days zero, 2, 5, 8, 11, 14, 17, 20, and 28.

Results

The intra-peritoneal stimulation of the Balb/c mice with pGPL very significantly alleviated the leukopenia induced by previous treatment with Adriblastine, to a degree comparable to that of mouse GM-CSF.

9. Test of phagocyte function—activity of pGPL in removal of colloidal carbon

This test enables the study of the dynamics of removal of particles of colloidal carbon from the blood by the phagocyte cells. The treated mice receive the test product in oral doses of 12 mg/kg on each of days −8, −5, and −2. The control mice receive only physiological serum. On day zero, each of the mice receive a single i.v. dose of colloidal carbon (Pelikan "Encre de Chine" black), in a 4% suspension in gelatin. The dose was 16 mg/100 g of body weight. Blood samples (0.025 ml each) were taken at times 0, 2, 4, 6, 8, 10, and 12 min. The samples are measured by spectrophotometry at wavelength 630 microns. This enables measurement of the remaining carbon particles in suspension in the blood.

Results

The stimulation of CDI mice with pGPL in oral doses of 12 mg/kg on each of days −8, −5, and −2 induced a significant increase in the clearance of colloidal carbon.

What is claimed is:

1. A pharmaceutical composition characterized in that it comprises, as an active ingredient, an extraction fraction, at least partially purified, of a polar glycopeptidolipid from *Mycobacterium chelonae,* or a derivative of a polar glycopeptidolipid of *M. chelonae,* which derivative is active as an immunostimulant.

2. A composition according to claim 1, characterized in that said at least partially purified fraction is a fraction soluble in methanol at +4° C.

3. A composition according to claim 1, characterized in that said at least partially purified fraction is a fraction which can be obtained by extraction of cells or cell walls of *M. chelonae* with the aid of a 2:1 chloroform-:methanol mixture at a temperature of 18°–50° C., and which fraction is soluble in methanol at 4° C.

4. A composition according to claim 1, characterized in that it comprises, as an active ingredient, at least one glycopeptidolipid of formula 1:

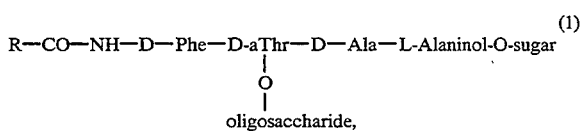

wherein
Phe represents phenylalanine,
aThr represents allo-threonine,
Ala represents alanine,
sugar is 3,4-di-O-methyl rhamnose, and
the oligosaccharide has the following structure: 3,4-di-O-methylrhamnose-rhamnose-6-deoxytalose, and
R—CO— is the acyl group of a fatty acid, wherein the 3,4-di-O-methylrhamnose groups are connected by a glycosidic link to the aThr and the alaninol, respectively, and wherein the C-terminal COOH group of the alanine is connected to the alaninol by an amide linkage.

5. A composition according to claim 4, characterized in that R—CO represents the acyl group of a fatty acid having at least 16 carbon atoms and less than 36 carbon atoms.

6. A composition according to claim 5, further characterized in that said fatty acid includes one or more double bonds, a branch, beta-hydroxy substituent, a beta-methoxy substituent, or a combination thereof.

7. A composition according to claim 1, characterized in that said derivative is a de-acetylated derivative.

8. A composition according to claim 4, characterized in that said at least one glycopeptidolips of formula (1) is obtained by synthesis or semi-synthesis.

9. A composition according to claim 1, characterized in that it is prepared in the form of gel capsules, tablets, powders, suppositories, gingival pastes, or creams or compositions adapted for nasal or conjunctival administration.

10. A composition according to claim 1, characterized in that it is prepared in the form of a suspension in a liquid pharmaceutical vehicle, or in the form of a lyophilizate.

11. A composition according to claim 1, characterized in that it further comprises an efficacious quantity of a preservative agent, or a surfactant, or a combination thereof.

12. A composition according to claim 1, characterized in that is comprises the active ingredient in the amount of 0.02–8%, based on the total weight of the composition.

13. A method of stimulating the immune system comprising administering to a mammal in need thereof an effective stimulating amount of a composition according to claim 1.

14. A method according to claim 12, wherein the mammal in need thereof is a patient suffering the immunosuppressive effects of anticancer therapies.

15. An immunostimulating glycopeptidolipid of formula 1:

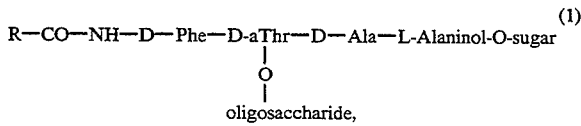

wherein
Phe represents phenylalanine,
aThr represents allo-threonine,
Ala represents alanine,
sugar is 3,4-di-O-methyl rhamnose,
the oligosaccharide has the following structure:
3,4-di-O-methylrhamnose-rhamnose-6-deoxytalose, and
R—CO— is the acyl group of a fatty acid, wherewith the 3,4-di-O-methylrhamnose groups are connected by a glycosidic link to the aThr and the alaninol, respectively, and wherein the terminal COOH group of the alanine is connected to the alaninol by an amide linkage.

16. A method of stimulating growth comprising administering to a mammal in need thereof an anabolic effective amount of a composition according to claim 1.

17. A method of preparing a vaccine comprising mixture an adjuvant effective amount of a composition according to claim 1 with an antigen.

18. A method of stimulating growth according to claim 16, wherein said anabolic effective amount is administered in a nutrient compositions.

* * * * *